(12) United States Patent
Nagy et al.

(10) Patent No.: US 6,788,072 B2
(45) Date of Patent: Sep. 7, 2004

(54) APPARATUS AND METHOD FOR SENSING PARTICLE ACCUMULATION IN A MEDIUM

(75) Inventors: Louis L. Nagy, Warren, MI (US); Warren Baxter Nicholson, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 54 days.

(21) Appl. No.: 10/341,567

(22) Filed: Jan. 13, 2003

(65) Prior Publication Data

US 2004/0135584 A1 Jul. 15, 2004

(51) Int. Cl.$^7$ .......................... G01R 27/32; G01N 15/04
(52) U.S. Cl. ..................... 324/639; 324/645; 324/698; 73/53.07
(58) Field of Search ................................. 324/639, 645, 324/637, 663, 642, 643, 698; 73/61.41, 61.71, 53.05, 53.07

(56) References Cited

U.S. PATENT DOCUMENTS

| | | | |
|---|---|---|---|
| 4,345,202 A | 8/1982 | Nagy et al. | 324/642 |
| 4,503,384 A | 3/1985 | Nagy et al. | 324/690 |
| 4,544,880 A | 10/1985 | Nagy et al. | 324/642 |
| 4,646,070 A | 2/1987 | Yasuhara et al. | 340/603 |
| 5,039,947 A | 8/1991 | Kraszewski et al. | 324/634 |
| 5,838,158 A | 11/1998 | Beck et al. | 324/636 |
| 6,268,737 B1 * | 7/2001 | Marszalek | 324/663 |
| 6,278,282 B1 | 8/2001 | Marszalek | 324/663 |
| 6,377,052 B1 * | 4/2002 | McGinnis et al. | 324/446 |
| 6,407,555 B2 | 6/2002 | Joshi et al. | 324/636 |
| 6,435,013 B1 | 8/2002 | Rodriguez et al. | 73/61.75 |

* cited by examiner

Primary Examiner—Anjan K. Deb
(74) Attorney, Agent, or Firm—Jimmy L. Funke

(57) ABSTRACT

A method and apparatus for detecting an accumulation of particles with a medium such as the soot content in diesel engine oil including generating a first waveform at a first frequency and a first voltage level to produce a standing wave having a voltage null point where at least a portion of the standing wave is passed within a portion of the oil. Generating a second waveform at a second frequency and a second voltage level to place a signal associated with a second voltage null point at a detection location for determining the signal's null point voltage level. The percentage soot content of the oil may be determined by taking the ratio of the difference between the first voltage and the second voltage over the null point voltage at the detection point. This ratio is indicative of the percentage soot content. The first and second waveforms may be produced by a variable frequency microwave source that is coupled with a coaxial cable have a probe affixed to its distal end for immersion in the oil. The probe may include a plurality of parallel wires affixed to the cable at one end with a conductive shorting plate at the other end. A processor may be configured for controlling the circuit of the apparatus and calculating the percentage soot content.

19 Claims, 3 Drawing Sheets

APPARATUS AND METHOD FOR SENSING PARTICLE ACCUMULATION IN A MEDIUM

BACKGROUND OF THE INVENTION

This invention relates in general to sensors and in particular to a high frequency apparatus and method for sensing the accumulation of particles having an electrical loss component such as soot in diesel engine oil.

During usage of a diesel engine, for example, the crankcase oil gradually experiences particle accumulation in the form of soot, which is a combustion by-product, in the combustion chamber of the engine. Portions of soot may then be transferred in small amounts to the crankcase oil. When the soot builds up to an unacceptable amount, such as a predetermined threshold percentage, the lubricating quality of the oil is diminished. When this occurs it may be necessary to change the crankcase oil whenever the soot content reaches an unacceptable value. For this purpose, it is desirable to measure the soot content percentage in the crankcase oil in order to detect the presence of the unacceptable percentage of soot.

Further, diesel engine oil is degraded by the presence of soot particles that increasingly accumulate with engine use. In addition, diesel oil is degraded as its additives are depleted and oil acidity is increased. It is becoming increasingly important for the efficient maintenance of diesel engines to have an on-board sensor that will accurately detect soot concentrations.

Microwave probes are known to be used for detecting soot in diesel engine oil such as the one disclosed in U.S. Pat. No. 4,345,202 issued to Nagy et al. Nagy discloses a microwave probe used to detect soot up to concentration levels of about five percent. This sensor used a single microwave frequency to characterize the real part of the relative permittivity for used diesel oil. From this data it was determined that the microwave probe could be used to measure the real part of the permittivity and thus determine soot content of up to about five percent. However, the more advanced diesel engines in today's markets frequently require detecting soot concentrations at levels up to about eight percent. This new requirement for detecting higher soot concentrations presents problems for existing electromagnetic sensors, which have not been able to accurately measure the soot content in diesel engine oils when soot content is greater than about four percent. Above a four percent soot concentration level, various small soot particles appear to agglomerate to form large electrically lossy particles. These agglomerate particles adversely affect the ability of these sensors to accurately measure soot concentrations because of the change in the particles geometry and increase in electrical losses.

It is known that even though soot particles are conductors rather than dielectric they can increase the relative permittivity or relative dielectric constant of a dielectric fluid, such as diesel oil for example, because very small conductive particles in a dielectric form what is commonly called an artificial dielectric. Thus, the proposition that the soot content of engine oil can be measured by measuring the relative permittivity of the oil is viable provided there are no other factors affecting the relative permittivity of the oil. The buildup of non-soot contaminants during engine service is one factor that can influence the relative permittivity. In addition, the formulation of the oil itself is a contributor to variable relative permittivity. That is, various engine oils have different compositions. There are synthetic, as well as natural petroleum bases, and there are various types of additives used by the numerous oil manufacturers. As long as these variables tend to influence the relative permittivity to a significant extent, then that relative permittivity parameter cannot be used as a measurement of soot content. That is, non-soot constituents of engine oil can contribute enough to relative permittivity measurements to make those measurements unsuitable for a measure of soot content.

Thus, it would be advantageous to provide an apparatus and method for accurately detecting the accumulation of particles having an electrical loss component, such as the soot content in diesel engine oil, at levels of up to about eight percent.

BRIEF DESCRIPTION OF THE INVENTION

An apparatus and method is provided for detecting soot content in diesel engine oil, especially at concentrations greater than about four percent. This may prevent oil from being changed prematurely, which may provide a significant economic gain to an operator of a fleet of vehicles, for example. Exemplary embodiments of the present invention allow for determining high-level soot content (i.e., up to and greater than four percent) based on the relative permittivity of the oil without the effects of non-soot contaminants adversely impacting that determination.

One exemplary embodiment of a method for detecting soot content in oil may comprise generating a first waveform at a first frequency and a first voltage level associated with this first frequency to produce a standing wave with a voltage null point at a first detector location with the null point having a first null voltage level. At least a portion of the standing wave will be passed within a portion of the oil having little to no soot content ("clean" oil). The first voltage level, associated with this first frequency, and first null voltage level may be used as a baseline for determining the soot content. A second waveform may be generated for an oil sample under investigation for soot content at a second frequency and a second voltage level associated with this second frequency to place a signal associated with the voltage null point at the first detector location with this null point having a second null voltage level. The soot content of the sampled oil may be determined by calculating the ratio of the difference between the second voltage level and the first voltage level and dividing this difference by the second null voltage level. The difference in the first and second voltage levels for generating the waveforms is associated with the magnitude of the diesel oil's dielectric characteristics while the difference in the null voltage levels is associated with the imaginary part (loss part) of the oil's dielectric characteristics. This ratio represents the normalization of the magnitude of the oil's dielectric characteristics to the losses associated with the soot concentration.

One exemplary embodiment of an apparatus for detecting soot content in oil may comprise a variable frequency microwave source coupled with a probe that is immersed within the oil. A microwave detector may be coupled with the probe to detect a signal level of a null voltage proximate the microwave detector. A microcontroller such as a processor may be provided that is coupled with the microwave source, the probe and the microwave detector. The processor may be configured to calculate a ratio of a difference between a first or baseline voltage level associated with a first standing wave and a second voltage level associated with a second standing wave, over the second null voltage level. The second voltage level and the second null voltage level may be determined in response to a change in a relative permittivity of the diesel oil and wherein the ratio is indicative of the percentage of soot content.

DETAILED DESCRIPTION OF THE INVENTION

It has been discovered by the inventors of the present invention that the soot content of diesel oil is proportional to the oil's $\in/\in''$ value at microwave frequencies where $\in$ represents the oil's total dielectric constant (i.e., $\in=\in'-j\in''$ where $\in'$ is the real part and $\in''$ is the loss part of $\in$) and $\in''$ represents the loss portion of the oil's total dielectric constant. For oils containing a low concentration of soot and hence low electrical loss (i.e., $\in''$ can be neglected), the measurement of the oil's dielectric total constant ($\in$) will provide a good approximation of $\in'$ (i.e., $\in=\in'$) that will then provide accurate information about soot content. When significant electrical loss exists in an oil (because of high soot concentrations), this loss will bias the measurement of $\in$ and must be taken into account for determining $\in'$. The present inventors have discovered that of dividing the loss component out of the calculations for determining changes in the oil's dielectric constant allows for accurately determining the percentage of soot content in the oil above four percent.

Figure 1:
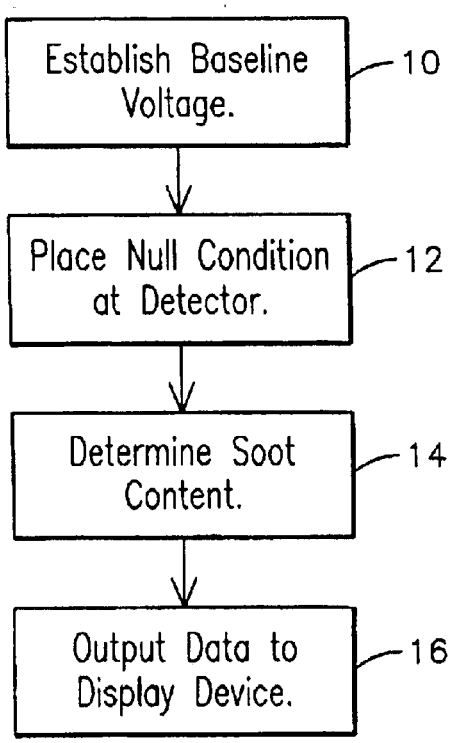
FIG. 1 is a flow chart illustrating one exemplary embodiment of a method of the present invention.

FIG. 1 illustrates a flow chart depicting one embodiment of a method of the present invention. Various exemplary embodiments of the present invention may be implemented using appropriately configured sensors such as the sensor system disclosed in U.S. Pat. No. 4,345,202 issued to Nagy et al., for example, which is specifically incorporated herein by reference in its entirety. Step 10 allows for establishing a first voltage level for generating a first frequency to produce a first waveform, such as a first standing wave, within at least a portion of diesel oil, for example, the standing wave having a voltage null point or condition placed at a known sampling or detection point. The sampling or detection point may be a point on a soot sensor for detecting voltage levels, such as with a conventional RF detector, for example. In one exemplary embodiment, the first voltage level may be a baseline voltage level and may be established in clean or fresh oil that has a zero or near zero soot content. For example, one embodiment allows for the baseline voltage level to be established in oil within the sump of a vehicle immediately or shortly after the oil has been changed. Another embodiment allows for the baseline to be established in oil prior to the oil being placed within the sump of a vehicle. Alternate embodiments allow for the baseline voltage to be established in a medium having measurable soot content that is greater than zero, for example, to measure further changes to that soot content.

Once establishing the baseline or first voltage level in oil having a zero or near zero soot content, it is desirable to periodically sample the oil to measure the soot content. This may be accomplished in one aspect of the present invention by establishing a second voltage level for generating a second frequency to produce a second waveform, such as a second standing wave, within at least a portion of the oil being sampled. This allows for, in step 12, shifting or placing the voltage null point or condition associated with the second standing wave at the known sampling or detecting point. In this respect, the voltage null point or condition will have moved from its original placement in step 10, when the oil was "clean", as a function of changes to the oil's dielectric properties. One exemplary embodiment of the present invention allows for placing the voltage null point in step 12 at the known microwave detection or sampling point after a vehicle's engine has run for a period of time so that the soot content in the engine's oil may be determined. The microwave detector may measure the first null voltage level associated with the original or first null point or condition and a second null voltage level associated with the null point or condition when the oil is being sampled for soot content. In one exemplary embodiment of the present invention, the soot content of the oil may be determined in step 14 by the equation:

$$\text{(second voltage level−first voltage level)/(second null voltage level)} \quad (1)$$

Step 16 allows for calculating data indicative of the percentage of soot content and outputting that data to a display device, which may be an indicator on the dashboard of a vehicle, for example.

Figure 2:
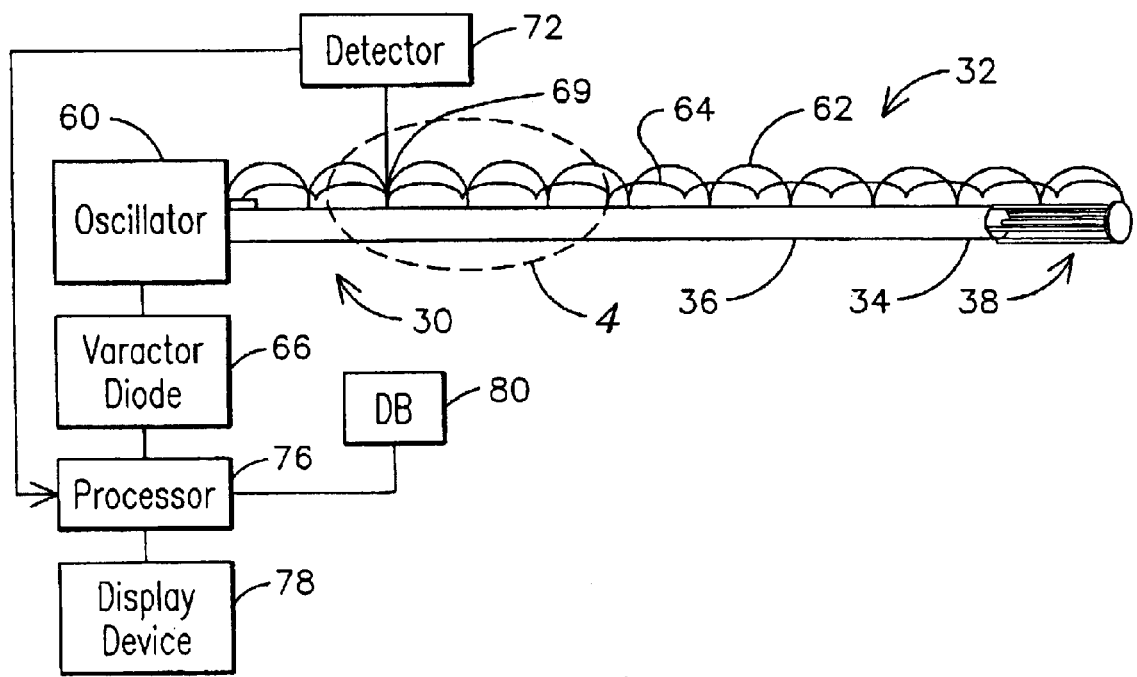
FIG. 2 is a schematic of an exemplary embodiment of a sensor system of the present invention.
Figure 3:
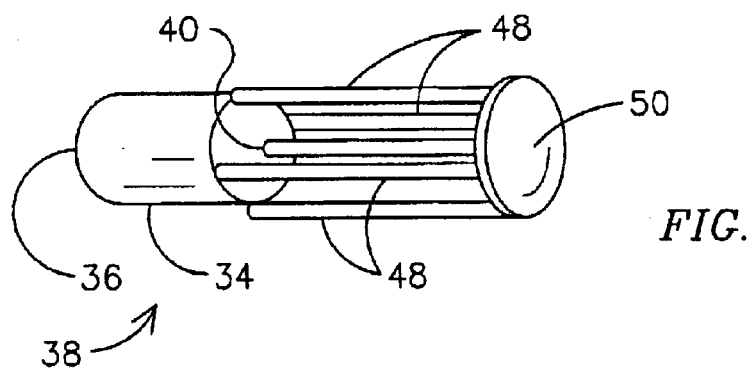
FIG. 3 is an enlarged view of an exemplary probe shown in FIG. 2.

FIG. 2 illustrates an exemplary embodiment of a sensor system 30 that may be used to determine the percentage of soot content of oil in accordance with one aspect of the present invention. System 30 may include a coaxial circuit such as an elongated conductor portion 32 configured to be inserted within a sump of an internal combustion engine, for example, so that the distal end 34 is immersed in oil that is contained within the sump. The portion 32 may be fabricated from a standard coaxial cable 36 having a probe portion 38 affixed to the distal end 34. Probe 38 may be constructed in a substantially similar manner and be made of substantially the same materials as disclosed and described in U.S. Pat. No. 4,503,384 issued to Nagy et al., for example. As shown best in FIG. 3, the probe 38 forms a non-resonant structure and may include a set of substantially parallel wires. In one exemplary embodiment the non-resonant structure may include a center wire 40, which may be the center wire of the coaxial cable 36, and four exterior wires 42. The exterior wires 42 may be joined at one end to the outer sheath of the coaxial cable 36 in a conventional manner, such as welding, soldering, etc. and at the other end to a conductive shorting plate 50 in a similar manner. The center wire 40 may also be connected to the shorting plate 50 in a conventional manner such as by welding. Thus, the probe 38 is a cage-like structure characterized by a plurality of spaced wires 40, 48 shorted at one end in an open configuration to allow oil to flow freely there between without pockets or other obstacles to trap oil or otherwise impede the free flow of oil.

Figure 4:
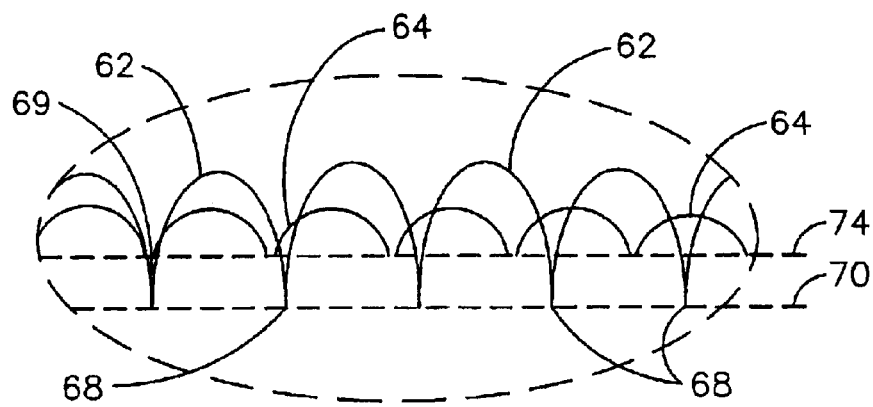
FIG. 4 is an enlarged view of a portion of the sensor system depicted in FIG. 2.

FIG. 2 also illustrates an oscillator 60 that may be used to generate the first waveform 62 and the second waveform 64. The first waveform 62 and second waveform 64 may be the first and second standing waves and may be formed by the respective forward waves from the oscillator 60 and the respective waves reflected from the plate 50. Oscillator 60 may be a conventional oscillator and in one exemplary embodiment may be a varactor-tuned oscillator that may produce variable frequencies in the microwave range, for example, between about 8 GHz and 12 GHz (X-band). It will be recognized by those skilled in the art that other frequencies may be used as a function of the medium under inspection, its dielectric properties and/or the electrical loss properties of the particles in the medium. A varactor diode 66 may be used to selectively vary the frequencies generated by the oscillator 60. As described above, first waveform 62 may be a standing wave generated at a first frequency by the oscillator 60 at a first voltage level where the first waveform 62 has a voltage null point or condition 68, as best shown in FIG. 4. Voltage null point 68 may be established at a fixed detection or sampling point 69 and has an associated first null voltage level 70.

As suggested above, the first voltage level may be used to establish a baseline voltage level for clean or fresh oil having a zero or substantially zero soot content. For example, the elongated conductor portion 32 may be inserted into an engine's sump so that the probe 38 is immersed in the oil. As the soot content changes in the oil over time, the null point 68 may shift longitudinally along the coaxial cable 36 in response to changes in the dielectric properties of the oil. One aspect of the present invention allows for oscillator 60 to produce the second waveform 64 at a second frequency and with a corresponding second voltage level so that that the null point 68 is moved back to or placed at the fixed detection or sampling point 69. A detector 72, which may be a microwave detector in one exemplary embodiment, may be used to detect a signal associated with this second null voltage level 74 for the oil undergoing soot content measurement. Detector 72 may also detect the first null voltage level 70. Data indicative of a signal level associated with the second null voltage level 74 may be transmitted from the detector 72 to a microcontroller such as processor 76. Processor 76 may be configured to calculate the soot content of the sampled oil base on Equation (1) as discussed above. Processor 76 may output data indicative of the percentage soot content to a display device 78, which in one exemplary embodiment may be a conventional indicator on the dashboard of a vehicle. A database 80 may be provided that allows for storing data associated with exemplary embodiments of the present invention. This data may be retrieved and processed by the processor 76.

Figure 5:
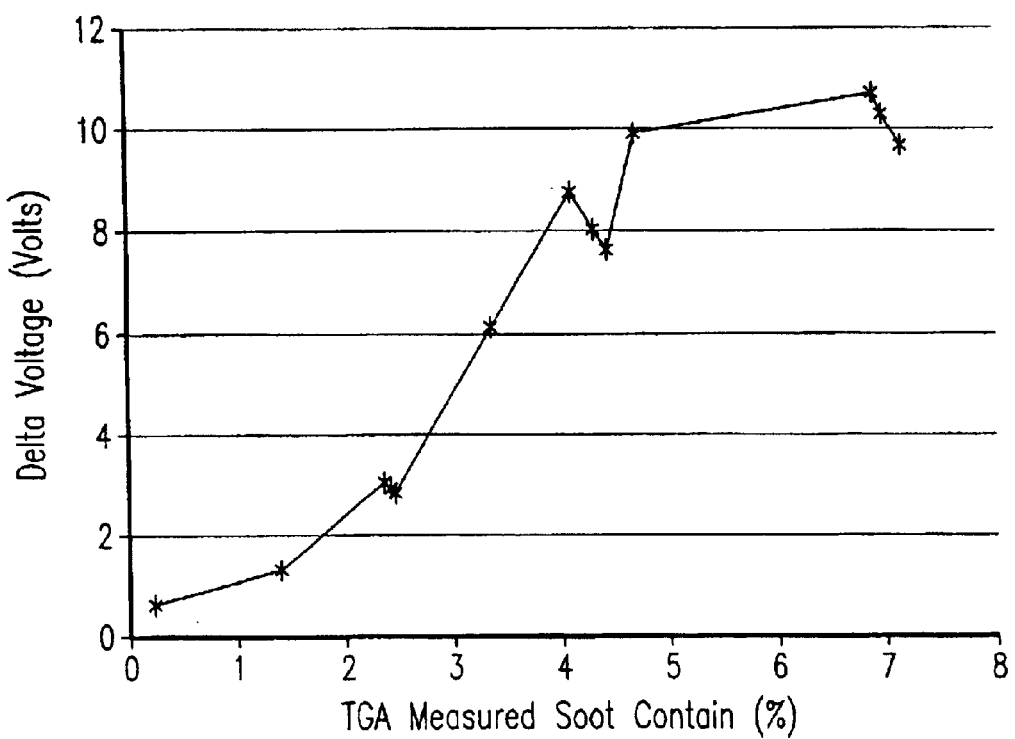
FIG. 5 is a graph plotting a change in voltage against a standard for measuring the percentage of soot content.
Figure 6:
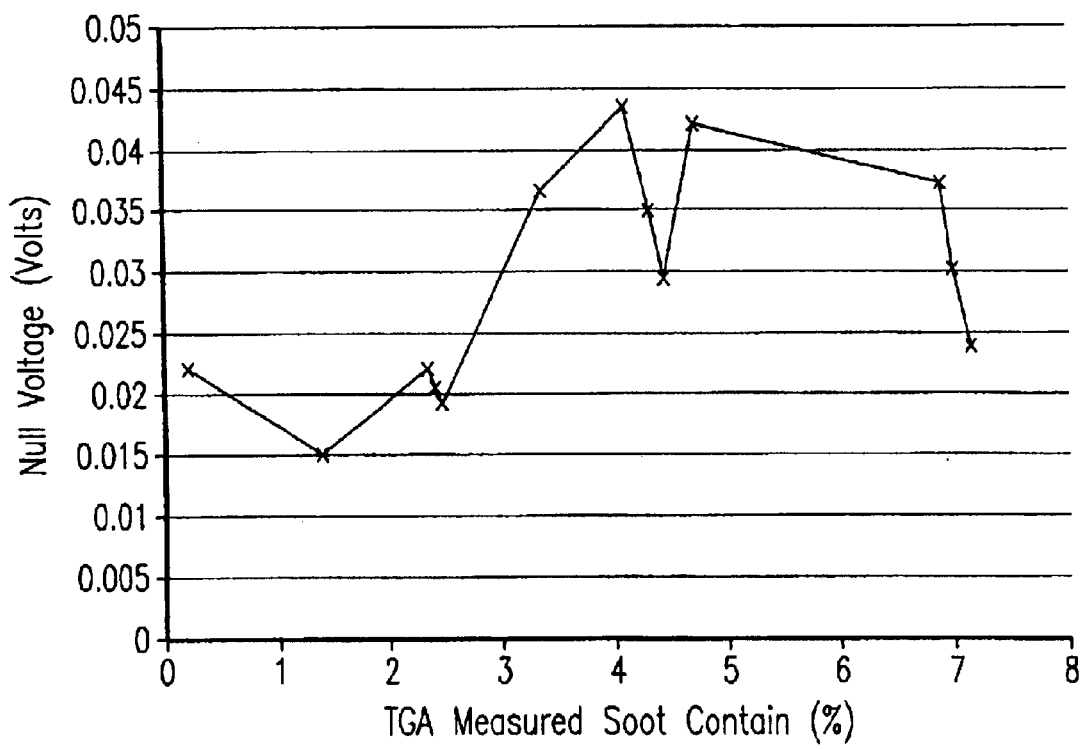
FIG. 6 is a graph plotting a null voltage against a standard for measuring the percentage of soot content.
Figure 7:
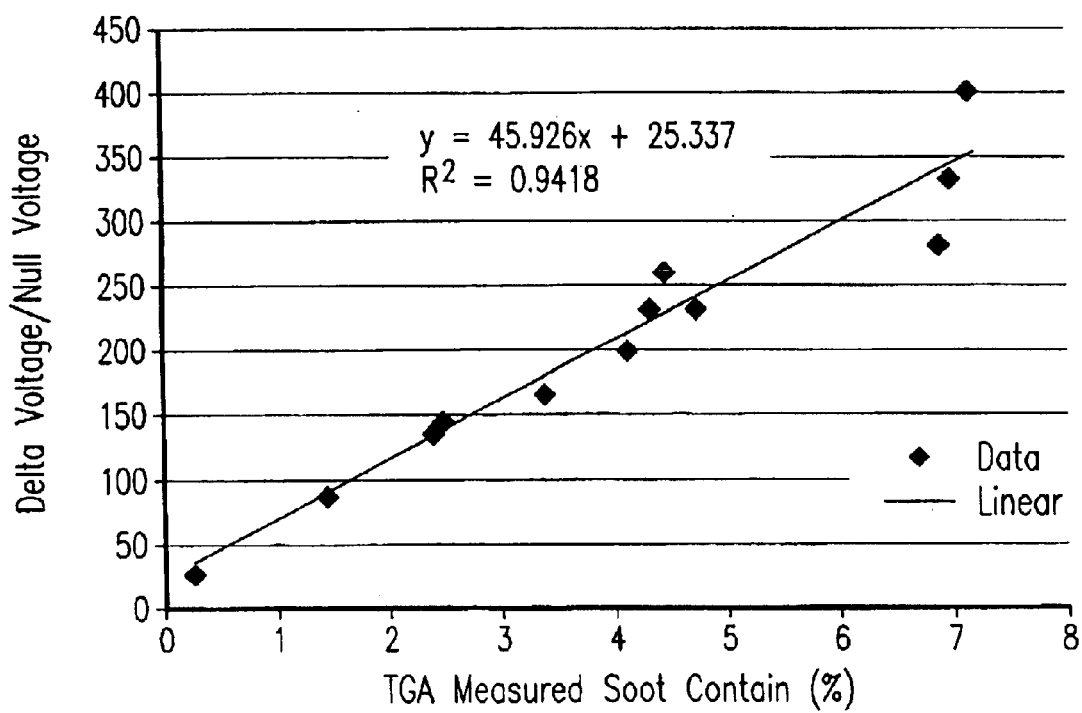
FIG. 7 is a graph plotting a change in voltage/null voltage against a standard for measuring the percentage of soot content.

It has been determined by the inventors of the present invention that a substantially linear relationship may be obtained by comparatively calculating the soot content of oil in accordance with aspects of the present invention and determining soot content by the generally accepted scientific technique of Thermogravimetric Analysis (TGA). FIGS. 5–7 demonstrate different exemplary functional relationships determined by the inventors of the present invention. FIG. 5 plots the change in the first voltage and the second voltage as determined in one aspect of the present invention against the percentage of soot content of the associated oil as measured using TGA. Similarly, FIG. 6 plots the null voltage as determined in one aspect of the present invention against the percentage of soot content of the associated oil as measured using TGA. FIG. 7 plots the change in the first voltage and the second voltage/the null voltage in accordance with one aspect of the present invention against the percentage of soot content of the associated oil as measured using TGA. The change in voltage/null voltage is shown as a ratio without units. One aspect of the present invention allows for configuring the processor 76 to calibrate the change in voltage/null voltage ratio to be in whatever units are desired provided that the selected units correspond to the percentage of soot content as shown in FIG. 7. Also, the change in the first voltage and the second voltage is proportional to the oil's dielectric constant and the null level voltage is proportional to the imaginary part (loss) of the oil's dielectric constant. The inventors have also determined that the ratio of the difference in voltages to the null voltage level as describe above is proportional to the soot content.

It will be understood by those skilled in the art that exemplary embodiments of the present invention may be embodied in the form of computer code and/or computer-implemented processes and apparatus for practicing those processes. While the preferred embodiments of the present invention have-been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

What is claimed is:

1. A method for detecting soot content in diesel engine oil, the method comprising:
   a) generating a first waveform at a first frequency and a first voltage level to produce a first standing wave having a first voltage null point, at least a portion of the first standing wave passing within a portion of the oil having a first state of soot content;
   b) generating a second waveform at a second frequency and a second voltage level to produce a second standing wave having a second voltage null point, at least a portion of the second standing wave passing within a portion of the oil having a second state of soot content;
   c) placing a signal associated with the second voltage null point at a detecting point; and
   d) determining the ratio of the difference between the second voltage level and the first voltage level over a voltage level associated with the second voltage null point, wherein the ratio is indicative of the second state of soot content.

2. The method of claim 1 further comprising:
   providing at least one frequency source for generating the first waveform and the second waveform.

3. The method of claim 2 wherein the at least one frequency source is a varactor-tuned microwave source configured to generate the first waveform and the second waveform.

4. The method of claim 1 wherein the first frequency and the second frequency are microwave frequencies.

5. The method of claim 1 wherein the first state of soot content is substantially zero and the first voltage level is measured when the first voltage null point is proximate the detecting point.

6. The method of claim 1 further comprising:
   repeating the steps a)–d) at predetermined intervals to determine the respective second states of soot content over a period of time.

7. The method of claim 1 wherein the first standing wave is produced within a coaxial conductor extending into the oil and a wavelength of the first standing wave is modified by a relative permittivity of the oil.

8. The method of claim 7 further comprising:
   detecting the modified wavelength; and
   the step of generating the second waveform comprising generating the second waveform in response to the modified wavelength.

9. The method of claim 1 further comprising:

outputting data indicative of the second state of soot content to a display device.

10. A method for detecting a relative permittivity of a medium to determine a percentage content in the medium of particles having an electrical loss component, the method comprising:

establishing a baseline voltage level when the percentage particle content of the medium is substantially zero, the baseline voltage level associated with a first standing wave at least a portion of which is passed within the medium;

varying the frequency of a microwave source to generate a second standing wave at least a portion of which is passed within the medium such that a null condition of the second standing wave is placed proximate a detection point;

determining a second voltage level associated with a frequency when the null condition of the second standing wave is proximate the detection point;

detecting a null voltage level of the null condition proximate the detection point; and determining a ratio of a difference between the second voltage level and the baseline voltage level over the null voltage level, the ratio being indicative of the percentage content of the particles.

11. The method of claim 10 further comprising:

selectively varying the frequency of the microwave source in response to movement of a first null condition associated with the first standing wave where the first null position will move from the detection point in response to a change in the relative permittivity of the medium.

12. The method of claim 10 further comprising:

outputting data indicative of the percentage particle content to a display device.

13. The method of claim 10 further comprising:

detecting the relative permittivity at predetermined intervals to determine the respective percentage content of particles in the medium; and determining whether to replace the medium with new medium based on the percentage of particle content of the medium.

14. The method of claim 10 further comprising:

varying the frequency of the microwave source with a varactor diode.

15. An apparatus for detecting a percentage of soot content in a quantity of diesel oil, the apparatus comprising:

a variable frequency microwave source;

a probe immersed within the oil;

a microwave detector; and a processor coupled with the microwave source, the probe and the microwave detector, the processor configured to calculate a ratio of a difference between a baseline voltage level associated with a first standing wave and a second voltage level associated with a second standing wave over a null voltage level, the second voltage level and the null voltage level determined in response to a change in a relative permittivity of the diesel oil and wherein the ratio is indicative of the percentage of soot content.

16. The apparatus of claim 15 further comprising:

a coaxial circuit coupling the microwave source to the probe.

17. The apparatus of claim 15 wherein the baseline voltage level is determined in a quantity of oil having a percentage soot content that is substantially zero.

18. The apparatus of claim 15 wherein the processor is configured to calculate the ratio at predetermined intervals so that the percentage soot content of the oil is detected a plurality of times over a period of time.

19. The apparatus of claim 15 wherein the apparatus is adapted to be inserted within a sump of an internal combustion engine so that the probe is immersed within the oil.

* * * * *